(12) United States Patent
Bergin et al.

(10) Patent No.: US 8,454,684 B2
(45) Date of Patent: Jun. 4, 2013

(54) HEART VALVE HOLDER FOR USE IN VALVE IMPLANTATION PROCEDURES

(75) Inventors: Cathleen A. Bergin, Hugo, MN (US); Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1066 days.

(21) Appl. No.: 11/888,915

(22) Filed: Aug. 2, 2007

(65) Prior Publication Data

US 2008/0071367 A1      Mar. 20, 2008

Related U.S. Application Data

(60) Provisional application No. 60/835,367, filed on Aug. 2, 2006.

(51) Int. Cl.
*A61F 2/24* (2006.01)
(52) U.S. Cl.
USPC ........................................... 623/2.11
(58) Field of Classification Search
USPC .............. 623/2.11, 2.15, 2.19, 1.11; 606/213, 606/215–218, 205, 207, 210
See application file for complete search history.

(56) References Cited

U.S. PATENT DOCUMENTS

| | | | |
|---|---|---|---|
| 4,106,129 A | | 8/1978 | Carpentier et al. |
| 4,655,218 A * | | 4/1987 | Kulik et al. .................... 606/207 |
| 4,865,600 A | | 9/1989 | Carpentier et al. |
| 4,990,151 A * | | 2/1991 | Wallsten ........................ 606/108 |
| 5,037,434 A | | 8/1991 | Lane |
| 5,089,015 A * | | 2/1992 | Ross .............................. 606/144 |
| 5,195,506 A * | | 3/1993 | Hulfish .......................... 600/204 |
| 5,423,856 A * | | 6/1995 | Green ............................ 606/215 |
| 5,476,510 A * | | 12/1995 | Eberhardt et al. ........... 623/2.11 |
| 5,478,353 A * | | 12/1995 | Yoon ............................. 606/213 |
| 5,716,401 A | | 2/1998 | Eberhardt et al. |
| 5,807,405 A * | | 9/1998 | Vanney et al. ............... 623/2.11 |
| 5,984,950 A * | | 11/1999 | Cragg et al. .................. 606/216 |
| 6,187,016 B1 * | | 2/2001 | Hedges et al. ................ 606/108 |
| 6,736,845 B2 * | | 5/2004 | Marquez et al. ............. 623/2.11 |
| 6,893,459 B1 * | | 5/2005 | Macoviak .................... 623/2.11 |
| 7,018,407 B1 | | 3/2006 | Wright et al. |
| 7,033,390 B2 | | 4/2006 | Johnson et al. |
| 7,169,172 B2 * | | 1/2007 | Levine et al. ................ 623/1.11 |

(Continued)

OTHER PUBLICATIONS

Medtronic Brochure, "A New Dimension—The Hancock II Bioprosthesis", Medtronic Inc., 1991, publication No. UC8903226EN, 8 pages.
Medtronic Brochure, "A New Light on the Hancock Bioprosthesis", Medtronic Inc., 1988, publication No. UC8801713EN, 13 pages.

*Primary Examiner* — Julian Woo
*Assistant Examiner* — Christopher L Templeton (57) ABSTRACT

A valve holder for a prosthetic valve having a stent comprising a stent base and multiple commissure posts projecting from the stent base, the valve holder including a connector hub, a plurality of legs connected to the connector hub, each leg having an elongate portion and a commissure post engaging plate, a sliding member slideably connected to each leg of the plurality of legs and positioned between the connector hub and the commissure post engaging plates of the plurality of legs and slideably positionable at a first position relative to the connector hub with the commissure post engaging plates in an uncompressed configuration and a second position relative to the connector hub with the commissure post engaging plates in a compressed configuration, and a handle extending from the connector hub.

14 Claims, 8 Drawing Sheets

U.S. PATENT DOCUMENTS

| | | |
|---|---|---|
| 7,189,258 B2 | 3/2007 | Johnson et al. |
| 7,722,641 B2 * | 5/2010 | van der Burg et al. ........ 606/216 |
| 8,038,704 B2 * | 10/2011 | Sherburne .................... 623/1.11 |
| 8,080,053 B2 * | 12/2011 | Satasiya et al. ............. 623/1.15 |
| 2001/0002445 A1 * | 5/2001 | Vesely ......................... 623/2.11 |
| 2004/0024451 A1 * | 2/2004 | Johnson et al. .............. 623/2.11 |
| 2004/0220655 A1 * | 11/2004 | Swanson et al. ............. 623/1.11 |
| 2005/0080431 A1 * | 4/2005 | Levine et al. ................. 606/108 |
| 2007/0088431 A1 * | 4/2007 | Bourang et al. ............. 623/2.11 |

* cited by examiner

HEART VALVE HOLDER FOR USE IN VALVE IMPLANTATION PROCEDURES

CROSS-REFERENCE TO RELATED APPLICATION

The present application claims priority to U.S. Provisional Application No. 60/835,367, filed Aug. 2, 2006, and titled "Heart Valve Holder For Use In Valve Implantation Procedures", the entire contents of which is incorporated herein by reference in its entirety.

TECHNICAL FIELD

The present invention relates generally to implantable valvular prostheses, and more particularly relates to a holding system or mechanism that can provide temporary prosthetic heart valve stent post deflection during implantation of valvular prostheses.

BACKGROUND OF THE INVENTION

Various types and configurations of prosthetic heart valves are used to replace diseased natural human heart valves. The actual shape and configuration of any particular prosthetic heart valve is dependent to some extent upon the valve being replaced (i.e., mitral valve, tricuspid valve, aortic valve, and pulmonary valve). In general terms, however, most prosthetic heart valve designs attempt to replicate the function of the valve being replaced and thus will include valve leaflet-like structures.

As used throughout this specification a "prosthetic heart valve having relatively flexible leaflets" or a "prosthetic heart valve" is intended to encompass bioprosthetic heart valves having leaflets made of a biological material as well as synthetic heart valves having leaflets made of a synthetic (e.g., polymeric) material. Either type of prosthetic heart valve can include a frame or stent or may have no such frame or stent. A stented prosthetic heart valve typically includes a stent having a substantially circular base, around which an annular suture material is disposed to form a sewing ring for suturing the prosthesis to heart tissue. The stent further typically includes at least two, but typically three, support structures extending from the stent base. These support structures are commonly referred to as stent posts or commissure posts. These posts typically are rigid yet somewhat flexible structures extending from the stent base, which are covered by a cloth-like material similar to that of the annular suture material or tissue. The stent or commissure posts define the juncture between adjacent tissue or synthetic leaflets otherwise secured thereto. Examples of bioprosthetic heart valves are described in U.S. Pat. No. 4,106,129 (Carpentier et al.), and U.S. Pat. No. 5,037,434 (Lane), the entire disclosures of which are incorporated herein by reference. These disclosures detail a conventional configuration of three leaflets, with one leaflet disposed between each pair of stent or commissure posts.

Implantation of a stented prosthetic heart valve presents certain technical challenges. For example, a prosthetic mitral valve is normally implanted by placing the prosthesis into the mitral valve annulus with the stent posts projecting blindly deep into the patient's left ventricle. However, due to a lack of visibility through the prosthetic valve, a surgeon can inadvertently loop sutures around the stent posts during suturing of the annular suture ring portion of the prosthesis. Similarly, the extending stent posts may undesirably "snag" on chordae or trabeculae inside the left ventricular cavity. To avoid these complications, various prosthetic valve holders have been designed that inwardly retract or deflect and hold the mitral prosthetic stent posts during implantation. Some of the available prosthetic mitral heart valve holders include an elongated handle and a holder mechanism that is secured to the sewing ring and adapted to inwardly deflect the stent posts upon rotation of the handle. An exemplary prosthetic mitral heart valve holder is described in U.S. Pat. No. 4,865,600 (Carpentier et al.). In addition, these concepts can apply to a prosthetic tricuspid valve.

For another example, Medtronic mitral valves are commercially available under the trade designation "Hancock", which valves are mounted to a holder providing a mechanism for inward deflection, as illustrated in the brochures: "A New Dimension—The Hancock II Bioprosthesis", Medtronic Inc., 1991, publication number UC8903226EN and "A New Light on the Hancock Bioprosthesis", Medtronic Inc., 1988, publication number UC8801713EN, both of which are incorporated herein by reference in their entireties. This holder includes a ratcheting spool that is mounted above the sewing ring and which is rotatable by means of an attached handle to pull lengths of suture inward, thereby pulling sutures extending downward though the commissure posts and between the commissure posts upward, to thereby deflect the commissure posts inward. In general, these prosthetic mitral heart valve holder devices are well-suited for mitral valve replacement because the mitral valve surgical site is relatively easily accessed, with minimal anatomical obstructions "above" or away from the implant site. Thus, the surgeon is afforded a large, unobstructed area for locating and maneuvering the handle as well as performing necessary procedural steps (e.g., suturing the annulus suture ring of the valve to the heart tissue) with minimal or no interference from the handle and/or mechanism.

Aortic and pulmonic prosthetic heart valve implantation, however, presents different constraints from those associated with mitral or tricuspid valve replacement because there is less room for the surgeon to maneuver during the surgery. In particular, depending upon the type of aortotomy performed, the surgeon may first have to pass the prosthesis through the sinotubular junction, which is typically smaller than the tissue annulus onto which the prosthetic heart valve will be sutured. Because the stent posts extend proximally toward the surgeon in aortic and pulmonic valve replacement (as opposed to the distal stent post direction associated with mitral and/or tricuspid valve replacement), the chances of inadvertently looping sutures about stent post(s) is minimal. However, the proximally extending stent posts associated with the stented prosthesis still can interfere with the various other maneuvers required of the surgeon.

In light of the above, it can be desirable to inwardly deflect the stent posts during implantation of the aortic and/or pulmonic prosthetic heart valve. Unfortunately, the above-described mitral and/or tricuspid prosthetic heart valve holders are of little value for aortic and pulmonic valve replacement procedures in that these holders attach on the inflow side of the valve and position the handle and holder to extend in a direction opposite from that of the stent posts. As such, the handle and holder would have to be removed in order to implant the aortic prosthetic heart valve. Certain approaches have been taken to correct this incompatibility by reconfiguring the holder and handle on the outflow side of the valve, as described, for example, in U.S. Pat. No. 5,476,510 (Eberhardt et al.) and U.S. Pat. No. 5,716,410 (Eberhardt et al.), the entire disclosures of which are incorporated herein by reference.

There is a continued need to provide different devices for assisting in the implantation of stented prosthetic heart valves that can be used in any area of the heart, including devices that can be used for implantation of aortic prosthetic heart valves. In particular, a need exists for a stent post deflection device that is simple and effective to use for areas of the heart that are typically difficult to access by the surgeon, such as for aortic heart valve replacement.

SUMMARY OF THE INVENTION

The present invention is directed to a valve holder attached to a bioprosthesis to assist the surgeon in valve implantation. In particular, the valve holder of the invention can be used for aortic valve replacement, and provides for temporary deflection of stent posts of the prosthesis, such as an aortic prosthetic heart valve. This deflection of the stent posts helps to ease the implantation process, and also increases the space available for the surgeon to manipulate the sutures and tie suture knots. The holder of the invention is attached near the tips of the stent posts, which thereby provides an open space between the commissures and behind the stent posts for easier access to the sutures, such as for knot tying which can also reduce the time required for implantation. Other benefits include, but are not limited to: reduced cardiopulmonary bypass time; reduced potential for injury to patient's aorta during knot tying; the ability to implant a larger valve and resulting hemodynamic benefit; increased visibility to knots and a resultant reduction in potential for paravalvular leakage; and potential for less damage to the prosthetic valve during knot tying due to insufficient access.

The valve holder of the invention includes stent posts that are preferably deflected prior to or after handle attachment via sliding of a collar relative to a plurality of locking strips. In particular, a collar serves to lock the holder and stent posts in their deflected positions until the holder is removed by cutting the suture or sutures that attach the stent posts to the holder. The amount of stent post deflection can be predefined to multiple predetermined deflection positions, where each of these positions reflects a certain distance between the stent post tip and the longitudinal axis of the handle of the valve holder. The amount that each stent post is deflected is preferably uniform across all stent posts for a particular implantation procedure, although it is possible that only some of the stent posts are deflected or that the stent posts are deflected by different amounts.

In one embodiment, a valve holder is provided for a prosthetic valve having a stent comprising a stent base and multiple commissure posts projecting from the stent base. The valve holder comprises multiple extending legs, each of which corresponds to one of the commissure posts, and a sliding member that is slideable along the extending legs to cause the commissure posts to move from an undeflected position to a deflected position. The holder further comprises a handle that is attachable and detachable from a connector hub, and the connector hub also can capture the ends of the extending legs that are spaced from the commissure posts. Each extending leg comprises an elongated portion and a commissure post engaging plate that is removably attachable to a commissure post of the prosthetic valve, such as with the use of a suture. The relationship between the extending legs and the sliding member preferably provides at least two positions for the commissure posts; an undeflected position and a compressed or deflected position, although a number of intermediate positions are also possible. The deflected position of the stent posts is a preferable configuration to allow positioning of the prosthetic valve during placement and securing of the prosthetic valve during surgery. The sutures that are holding the commissure posts of the stent to the commissure post engaging plates may then be severed and the valve holder can be removed from the patient.

The invention includes a method of installing a prosthetic valve in a patient, the prosthetic valve having a stent comprising a stent base and multiple commissure posts projecting from the stent base. The method comprises the steps of: providing a valve holder comprising a connector hub, a plurality of legs connected to the connector hub, each leg comprising an elongate portion and a commissure post engaging plate, and a sliding member slideably connected to each leg of the plurality of legs and positioned between the connector hub and the commissure post engaging plates of the plurality of legs. The method further includes positioning the sliding member at a first position relative to the connector hub with the commissure post engaging plates in an uncompressed configuration, attaching each of the commissure posts to one of the commissure post engaging plates, moving the sliding member relative to the connector hub to a second position relative to the connector hub to position the commissure post engaging plates in a compressed configuration, positioning the valve holder with the attached valve at an implantation site of a patient, suturing the valve to tissue of the patient, detaching the valve from the valve holder, and removing the valve holder from the patient.

In another aspect of the invention, a valve holder is provided for a prosthetic valve having a stent comprising a stent base and multiple commissure posts projecting from the stent base. The valve holder comprises a connector hub, a plurality of legs connected to the connector hub, each leg comprising an elongate portion and a commissure post engaging plate, a sliding member slideably connected to each leg of the plurality of legs and positioned between the connector hub and the commissure post engaging plates of the plurality of legs and slideably positionable at a first position relative to the connector hub with the commissure post engaging plates in an uncompressed configuration and a second position relative to the connector hub with the commissure post engaging plates in a compressed configuration. The valve holder further comprises a cutting sleeve having an outer tubular structure that at least partially surrounds the connector hub and sliding member, and a handle extending from the connector hub. The cutting sleeve may further include multiple cutting ribs extending from an inner surface of the cutting sleeve.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
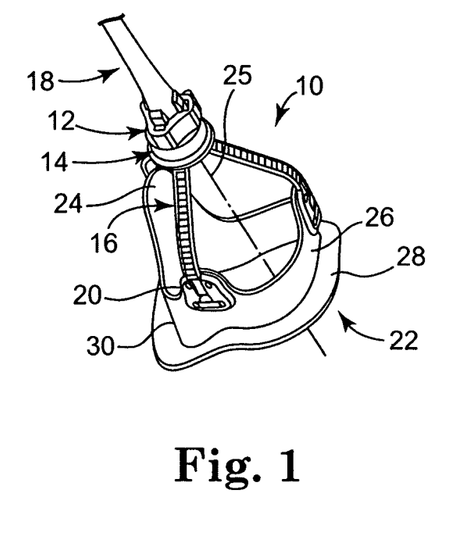
FIG. 1 is a perspective view of one embodiment of a portion of a valve holder of the invention, where the valve holder is attached to the top of the stent posts of a prosthetic heart valve, which posts are shown in their undeflected condition.
Figure 2:
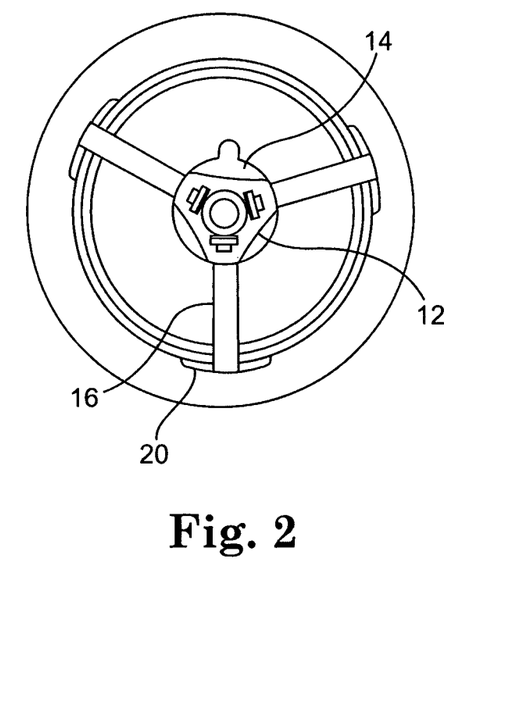
FIG. 2 is a top view of the valve holder of FIG. 1.

Referring now to the Figures, wherein the components are labeled with like numerals throughout the several Figures, and initially to FIGS. 1 and 2, a perspective view of one embodiment of a portion of a valve holder 10 of the invention is illustrated. The valve holder 10 generally includes a connector hub 12 and a sliding member 14, which are both attached to three extending legs 16. The extending legs 16 each include a commissure post engaging plate 20 that is attachable to the top portion of one of three commissure posts or stent posts 24 of a prosthetic heart valve 22, which stent posts 24 are shown in their undeflected condition in FIG. 1.

A handle 18 extends from one side of connector hub 12 and is preferably attachable to and detachable from the connector hub 12 at a distal end of the handle 18. In one preferred embodiment, the connection between the handle 18 and connector hub 12 is accomplished via a threaded connection, where the end of the handle 18 has outer threads that are compatible for connection with inner threads of a generally central opening in connector hub 12. However, the handle 18 may be attachable to the connector hub 12 in a number of different ways that allow the surgeon to attach and detach these two components with relatively minimal effort, when desired. The handle 18 can be made of stainless steel or another suitably rigid, sterilizable material. Exemplary handle connections can incorporate a pivot joint to enable optimum positioning of the handle and/or use a shape memory material (e.g., nitinol). Another exemplary embodiment of the handle may additionally include a reduced diameter portion along its length for enabling the handle to be bent to a desired angle during the valve implant procedure. Commercially available handles that may be used include those available from Medtronic Inc. of Minneapolis, Minn. under the trade designation "Mosiac" and "Hancock II."

As referred to herein, the prosthetic heart valves (e.g., heart valve 22) used in accordance with the devices and methods of the invention may include a wide variety of different configurations, such as a prosthetic heart valve having tissue leaflets or a synthetic heart valve having polymeric leaflets, and can be specifically configured for replacing any heart valve. That is, while much of the description herein refers to replacement of aortic valves, the valve holder of the invention can also generally be used for replacement of pulmonic valves, for use as a venous valve, or to replace a failed bioprosthesis, such as in the area of an aortic valve or mitral valve, for example. In any case, exemplary prosthetic heart valves 22 used with the present invention generally include a stent 26 including a base from which three stent posts or commissure posts 24 extend. All or a portion of the stent 26, including the stent posts 24, is preferably covered by a flexible covering 30, which may be a fabric, polymer, cloth or tissue material to which leaflets (not shown) of the heart valve 22 can be sewn. Further, as is known in the art, the internal structure of each of the stent posts 24 is formed of a stiff but resiliently bendable material. This construction allows the stent posts 24 to be deflected from the orientation shown in FIG. 1 to a deflected orientation by the application of an external force. Once this external force is removed or reduced, the stent posts 24 can then move back toward the orientation shown in FIG. 1.

Figure 3:
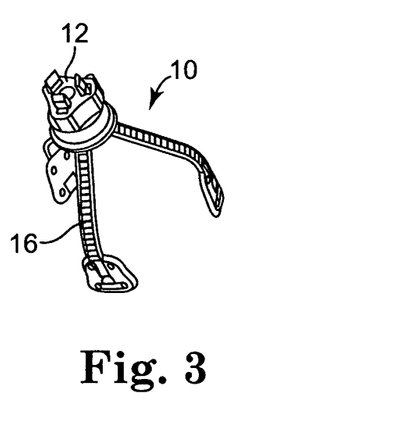
FIG. 3 is another perspective view of an embodiment of a valve holder of the invention, without the heart valve shown in FIG. 1.
Figure 4:
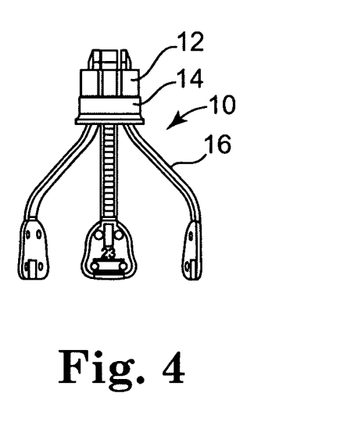
FIG. 4 is a front view of the valve holder of FIG. 3.

Referring now to FIGS. 3 and 4, two views of valve holder 10 are shown, without any corresponding heart valve 22. In these Figures, the connector hub 12 and sliding member 14 are shown in the position they will typically be in when their corresponding stent posts are not deflected. That is, the valve holder 10 is assembled as shown in these figures, which is the configuration that the valve holder 10 will be in when extending legs 16 are attached to stent posts of a heart valve. Thus, the extending legs 16 are molded or formed so that their positional relationship allows them to be assembled into valve holder 10 that is capable of providing the deflection of stent posts contemplated by the invention, which is described in further detail below.

FIGS. 5-8 provide multiple views of an exemplary embodiment of an extending leg 16 of the invention, which includes an elongated portion 32 having a proximal end 34 and a distal end 36. Elongated portion 32 further includes a series of teeth 38 that extend from a base portion 40. Each of the teeth 38 includes at least an angled surface 42 and a locking edge 44. All of the teeth 38 are preferably identical to each other along the length of a particular elongated portion 32, although they may be somewhat different in size or shape from each other, as long as the teeth are engageable with other components of the system in accordance with the invention. Thus, the locking edge 44 of each tooth 38 is preferably generally parallel to the locking edge 44 of each adjacent tooth 38 along the length of the elongated portion 32.

Extending leg 16 further includes a commissural post engaging plate 20 extending from proximal end 34 of elongated portion 32. Plate 20 may be integrally molded with elongated portion 32, or may instead be a separate component that is adhered or otherwise attached to elongated portion 32. Plate 20 is sized and shaped for attachment to a stent post of a heart valve via a pair of upper apertures 46, 48 and a pair of lower apertures 50, 52. The stitching configuration for attaching the plate 20 to a stent post preferably provides a secure attachment between the plate 20 and a corresponding stent post, yet allows for easy release (i.e., requires low removal force) with a single cut of the suture material.

One exemplary sequence for removably attaching the plate 20 to a stent post 24 includes using a single piece of suture material that is first inserted from a back surface 56 toward a front surface 54 of plate 20 through aperture 52. In this description, such a direction of the suture is described as being "up" (i.e., when the suture is moving from the back surface 56 toward the front surface 54) and is considered to be "down" when moving in the opposite direction (i.e., from the front surface 54 toward the back surface 56). In that regard, the suture is then moved across the plate 20 and inserted down into aperture 50, then through the fabric of the stent to which the plate 20 is being attached and up through the aperture 48. The suture is then extended across plate 20 and inserted down into aperture 46, then through the fabric of the stent and up through the aperture 52. The suture is again extended across the plate 20 and inserted down into aperture 50, thereby providing a double length of suture between aperture 50 and aperture 52. The end of the suture that is extending from aperture 52 and the other end of the suture that is extending from aperture 50 will both be protruding from the back surface 56 of plate 20, which back surface 56 includes a channel or recess 58 (see FIG. 8). To secure the suture, the two free suture ends will then be tied or knotted to each other so that when they are tightened, the knot will be pulled toward the back surface 56 of plate 20 and be positioned adjacent to or within the channel 58 of the back surface 56 to provide a relatively streamlined profile for the assembly.

Figure 7:
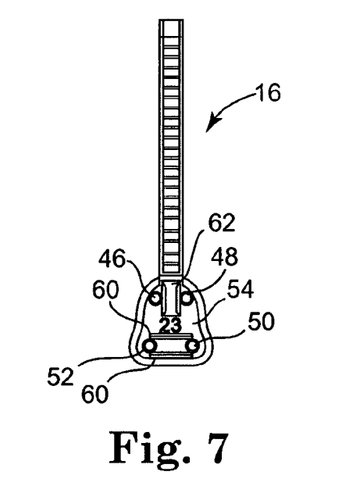
FIG. 7 is a front view of the extending leg of FIG. 5.
Figure 8:
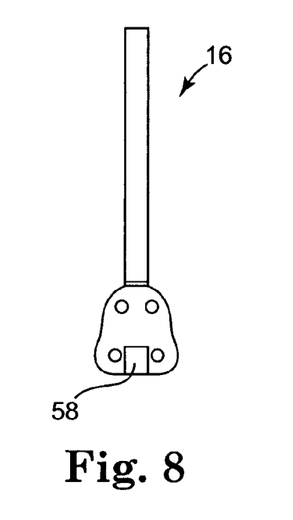
FIG. 8 is a back view of the extending leg of FIG. 5.
Figure 9:
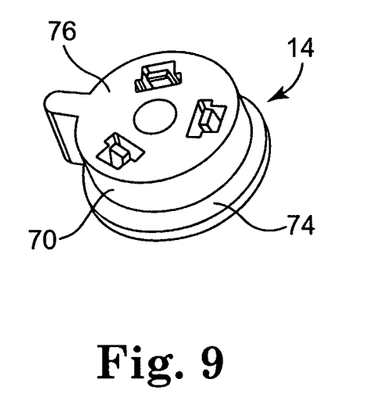
FIG. 9 is a perspective view of a sliding member of the valve holder of FIG. 3.
Figure 10:
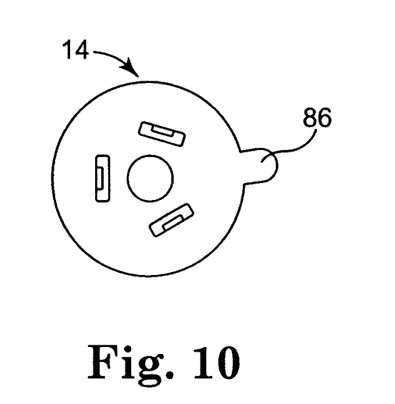
FIG. 10 is a bottom view of the sliding member of FIG. 9.

This embodiment of plate 20 further includes a guiding recess 62 positioned adjacent to and between apertures 46, 48. Guiding recess 62 is essentially recessed into the front surface 54 and provides a tactile guide to direct the surgeon to the preferred location for cutting the suture material when it is desired to detach the plate 20 from the stent post to which it is attached. That is, the recess 62 is detectable by the surgeon simply by feeling for the sutures and a corresponding recess, which corresponds with one exemplary cut point for the suture material. In order to lessen the possibilities that the surgeon will additionally or alternatively cut the suture unintentionally at the location between apertures 50, 52, plate 20 is provided with a pair of protective ridges 60 positioned adjacent to and on the outside of apertures 50, 52. Ridges 60 will make it difficult for a cutting tool that is moving from the top pair of apertures 46, 48 toward the lower pair of apertures 50, 52 to sever the suture between apertures 50, 52 since the cutting tool will come into contact with one of the ridges 60 before contacting the suture.

It is understood, however, that this described number and placement of apertures and ridges is only one of a number of aperture and ridge configurations that can be provided for a commissural post engaging plate of the invention. For example, more or less than four apertures may be used and/or arranged in a different pattern than that described above, more or less than two guide ridges and a guiding recess can be used, and/or different suture handling mechanisms can be provided instead of or in addition to guide ridges. In addition, the use of a commissure post engaging plate is not the only configuration contemplated for attachment of an extending leg to a stent post. Rather, the extending leg may include a wide variety of different end portion configurations that provide a secure end portion for attachment to a stent post, yet are reasonably small so as to not interfere with implantation of the heart valve.

Figure 5:
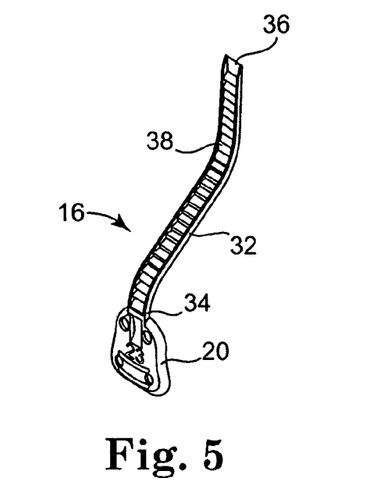
FIG. 5 is a perspective view of one extending leg of the valve holder of FIG. 3.
Figure 6:
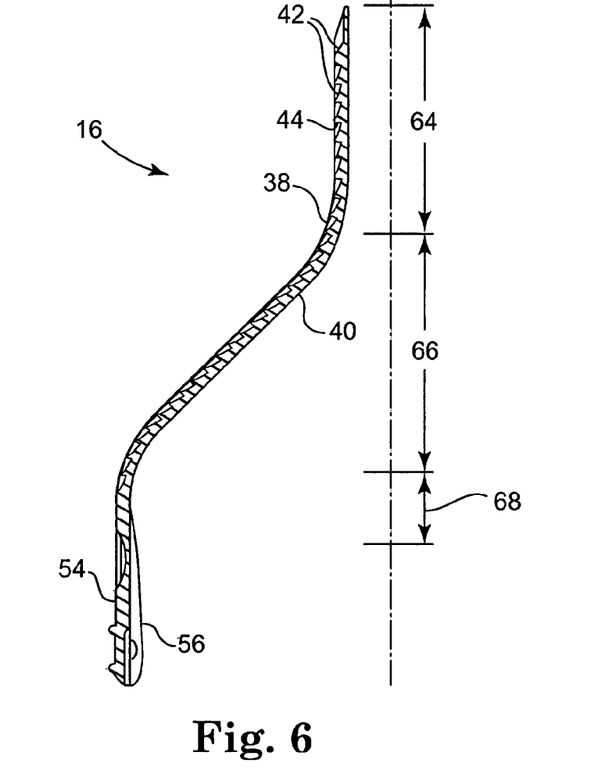
FIG. 6 is a cross-sectional side view of the extending leg of FIG. 5.

As is best illustrated in FIGS. 5 and 6, elongated portion 32 of extending leg 16 includes a profile having a first straight portion 64, an angled portion 66, and a second straight portion 68, with curved transition sections between each of these straight and angled portions. The lengths and/or angles of the portions of extending leg 16 are selected to provide a device that is manageable in size for the user, yet provides the desired amount of deflection for the stent posts, as will be described herein relative to the operation of the device. Each elongated portion 32 may be formed generally into the shape shown and may be relatively rigid to keep such a shape, or the elongated portion 32 can instead be relatively flexible in its construction so that it only generally takes the shape shown and described but can vary at least somewhat from this shape by manipulating the extending leg 16. The amount of flexibility of the elongated portions 32 can be selected by providing a different configuration for the material, varying the thickness of the material from which it is made, and the like. In addition, the elongated portions 32 may be provided with or without side rails, where the side rails will typically provide a higher level of stiffness to the elongated portions 32.

Referring now to FIGS. 9-12, multiple views of an exemplary embodiment of a sliding member 14 of the invention are illustrated. Sliding member 14 includes a generally cylindrical body 70 having any desired height that provides the desired structural support for the extending legs when the device is assembled, while minimizing the overall size of the device. A lip portion 74 extends from the bottom of body 70 and has a diameter that is at least slightly larger than that of body 70 to provide a contact or gripping surface for the user. Body 70 further includes three slots or apertures 72a, 72b, 72c that extend from a top surface 76 of body 70 through the thickness of body 70 and lip portion 74. One exemplary spacing of the slots 72a, 72b, 72c from each other around the top surface 76 is illustrated generally in FIG. 11, where slot 72a is positioned at an angle of 105 degrees from slot 72b, slot 72b is positioned at an angle of 120 degrees from slot 72c, and slot 72c is positioned at an angle of 135 degrees from slot 72a. These angular locations and spacings of the slots 72a, 72b, 72c from each other can be selected to correspond with the spacing of the leaflets from each other in an aortic valve, for example, which therefore results in the unequal spacing described above. However, it is understood that the spacing of the slots 72a, 72b, 72c from each other can vary widely from the relationships illustrated in FIG. 9, and that the angles between adjacent slots may be identical. Further, if a valve holder includes more or less than three legs (i.e., as may be used with a prosthetic valve having more or less than three leaflets), the spacing of the slots from each other can be chosen to accommodate a patient's anatomy, certain valve characteristics, and the like.

Figure 11:
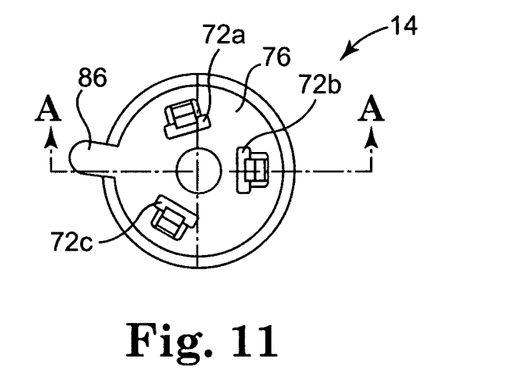
FIG. 11 is a top view of the sliding member of FIG. 9.
Figure 12:
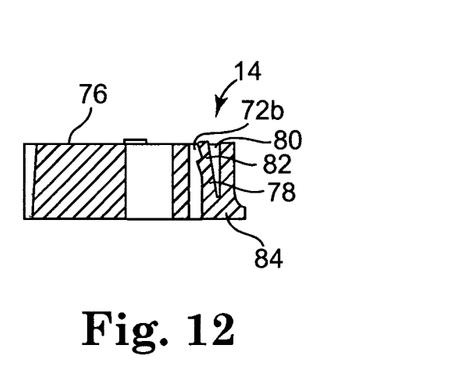
FIG. 12 is a cross-sectional side view of the sliding member of FIG. 11, taken along section line A-A.
Figure 13:
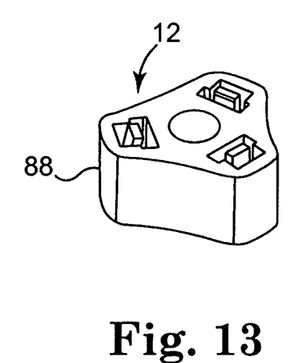
FIG. 13 is a perspective view of a connector hub of FIG. 3.
Figure 14:
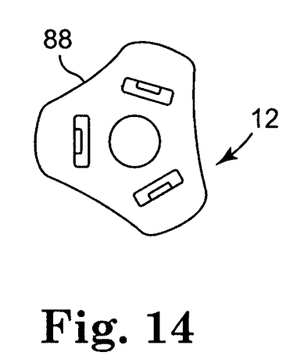
FIG. 14 is a bottom view of the connector hub of FIG. 13.
Figure 15:
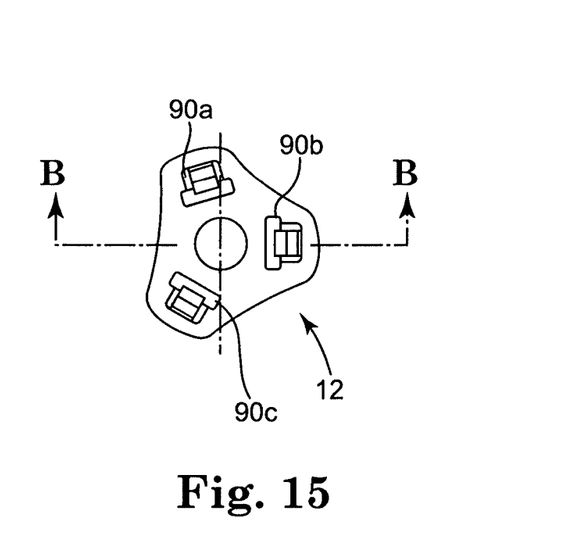
FIG. 15 is a top view of the connector hub of FIG. 13.

Each of the slots of the cylindrical body 70 are provided to accept the elongated portion of an extending leg, and generally are provided to allow one-way movement of an extending leg through the slot until the extending leg is locked in place relative to the body 70. In that regard, an exemplary slot configuration 72b is best illustrated in FIGS. 11 and 12, which show a spring arm 78 extending from a base 84 and comprising an engaging surface 82. A gap 80 is provided adjacent to the spring arm 78, which allows movement of the spring arm 78 toward and away from the outer surface of body 70. When the valve holder 10 is assembled as illustrated in FIG. 1, for example, an elongated portion 32 of an extending leg 16 will be positioned within the slot 72b. In order to deflect a stent post to which the extending leg will be attached, sliding member 14 will be moved toward the heart valve, which effectively will cause the teeth 38 of the extending leg 16 to move through the body 70 and toward the top surface 76. The angled surface 42 of each tooth 38 will ride along the inner surface of the spring arm 78 in a compression type action, thereby pushing spring arm 78 toward the outer surface of body 70 and decreasing the size of the gap 80. This movement will continue until the locking edge 44 of tooth 38 engages with engaging surface 82 of spring arm 78, thereby locking the extending leg 16 relative to the slot 72b. This movement can be repeated a number of times in a ratcheting type action with multiple teeth of the extending leg until the desired deflection of the stent posts of a heart valve is achieved.

Sliding member 14 further can include an optional indicator portion 86, which may be particularly useful in cases where the commissure posts are not equally spaced from each other. This indicator portion 86 can be used by the surgeon and/or other operating room personnel as an aid to properly orienting the valve holder 10 relative to a valve and/or other components or anatomical features. In the exemplary embodiment of FIGS. 9-11, the indicator portion 86 is positioned generally in the center of the space between adjacent slots 72a, 72c. This provides a visual and tactile indicator that the spacing between adjacent slots in this area is 135 degrees (i.e., the largest spacing between adjacent slots), which can help the surgeon in orienting the device.

Referring now to FIGS. 13-16, multiple views of one exemplary embodiment of a connector hub 12 of the invention are illustrated. Connector hub 12 generally includes a body 88 that is generally triangular or tri-lobed in shape. Body 88 further includes three slots or apertures 90a, 90b, 90c that extend through body 88. It is preferred that the slots in body 88 are generally in alignment with the slots in cylindrical body 70 for a particular valve holder 10, and that all of the slots in both connector hub 12 and sliding member 14 engage with the teeth 38 of the extending legs 16 of the same valve holder 10. One exemplary spacing of the slots 90a, 90b, 90c from each other around the top surface of body 88 is illustrated generally in FIG. 15, where slot 90a is positioned at an angle of 105 degrees from slot 90b, slot 90b is positioned at an angle of 120 degrees from slot 90c, and slot 90c is positioned at an angle of 135 degrees from slot 90a. These angular locations and spacings of the slots 90a, 90b, 90c from each other can be selected to correspond with the spacing of the leaflets from each other in an aortic valve, for example, which therefore results in the unequal spacing described above. However, it is understood that the spacing of the slots 90a, 90b, 90c from each other can vary widely from the relationships illustrated in FIG. 15, and the angles between adjacent slots may actually be identical. Further, if a valve holder includes more or less than three legs (i.e., as may be used with a prosthetic valve having more or less than three leaflets), the spacing of the slots from each other can be chosen to accommodate a patient's anatomy, certain valve characteristics, and the like.

Figure 16:
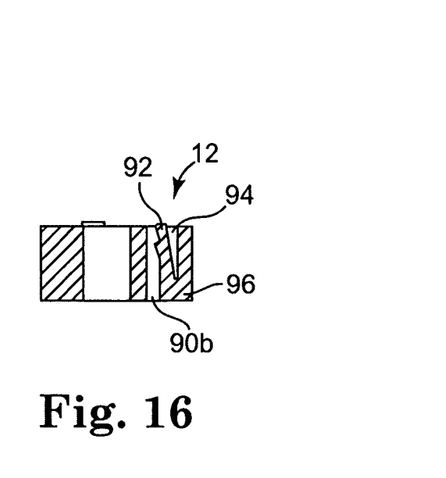
FIG. 16 is a cross-sectional side view of the connector hub of FIG. 15, taken along section line B-B.

As with the cylindrical body 70, each of the slots of the body 88 are provided to accept the elongated portion 32 of an extending leg 16, and generally are provided to allow one-way movement of an extending leg 16 through the slot 90a, 90b, or 90c until the extending leg 16 is locked in place relative to the body 70. In that regard, an exemplary slot configuration 90b is best illustrated in FIG. 16, which shows a spring arm 92 extending from a base 96 and a gap 94 adjacent to the spring arm 92. The slots of the body 88, along with the spring arm 92, are configured to essentially function in the same way as the slots 72a, 72b, 72c of the body 70 described above (i.e., a ratcheting action); thus, the same description of the exemplary ratcheting action of the slots of cylindrical body 70 applies similarly to the functioning of the slots 90 of the body 88.

As shown and described, the shape of body 88 of connector hub 12 is generally triangular or tri-lobal, which gives the user more physical clearance to access an adjacent sliding member 14. In particular, when the connector hub 12 is positioned on top of the sliding member 14, such as is illustrated in FIG. 2, the user will be able to contact the top surface of sliding member 14 in the relatively flat areas between the lobes of the body 88 without also pressing on the surface of connector hub 12. In this way, it can be easier to slide the sliding member 14 away from or relative to the connector hub 12. However, it is contemplated that the outer shape of body 88 can have another shape, such as another shape that provides clearance to the sliding member to press it toward the engaging plates 20, or a cylindrical shape to match the outer cylindrical shape of a sliding member 14, for example.

Figure 17:
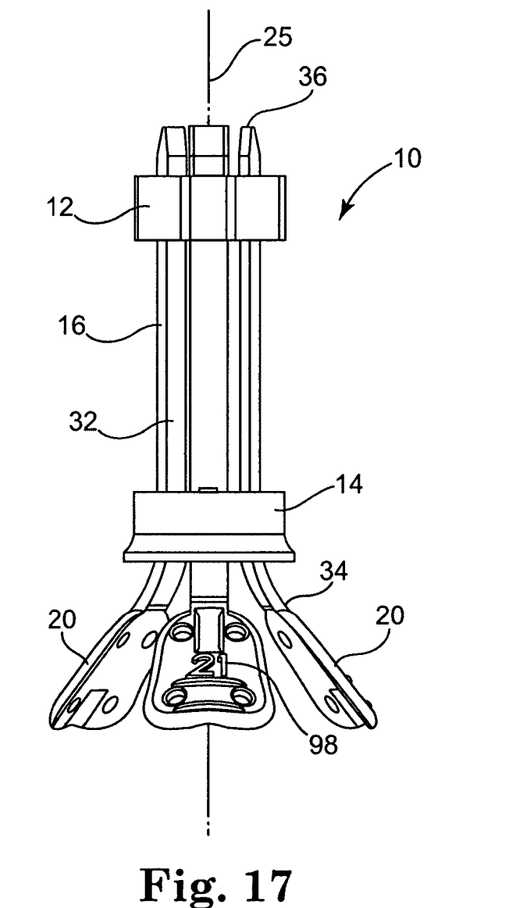
FIG. 17 is a front view of the valve holder of FIG. 3, with the sliding member positioned so that the commissure post engaging plates are in their compressed configuration.

FIG. 17 illustrates the valve holder 10 with the sliding member 14 spaced from the connector hub 12, which is one configuration of these components when the stent posts of a heart valve are in their compressed or deflected condition. As shown, sliding member 14 is positioned relatively close to the proximal end of the elongated portion 32 of the extending legs 16, which thereby pulls the commissural post engaging plates 20 closer to each other and to a longitudinal axis 25 of the valve holder (which axis is also illustrated in FIG. 1). In this way, the stent posts will be deflected or compressed toward each other, such as for insertion of the device into a patient. In accordance with the invention, the amount of compression of the stent posts can thus be determined by the amount that the sliding member 14 is moved toward the proximal end 34 of the elongated portion 32. Thus, the number of possible positions of the stent posts is dependent upon the number of teeth on the extending legs.

Commissure post engaging plates 20 may optionally include indicia 98 on their outer faces. The indicia 98 may provide information about the sizing of the device, for example, and may be provided on the surface in a number of known ways, such as by engraving, etching, molding or otherwise modifying the surface of the plates 20. Alternatively, the indicia 98 may be adhered, welded, or otherwise attached to the outer surface of the plates 20. In addition, it is contemplated that markings can be placed on the holder to indicate the largest stent opening and/or various degrees of deflection, cut points, valve size, handle insertion or deflection release points.

Figure 18:
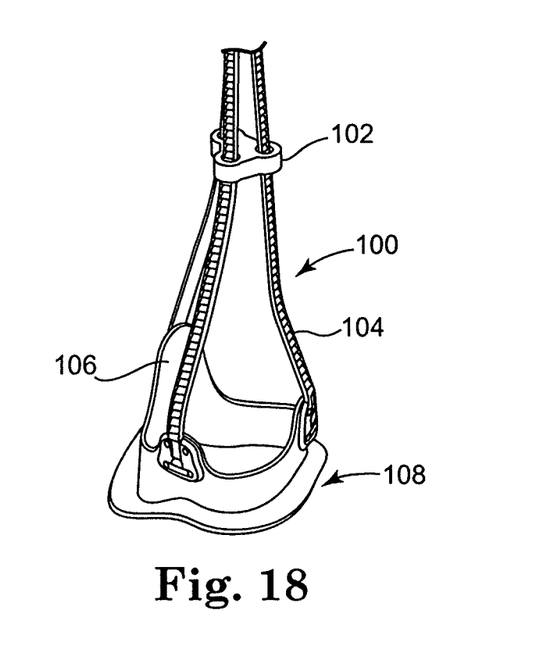
FIG. 18 is a perspective view of another embodiment of a valve holder of the invention, where the valve holder is attached to the top of the stent posts of a prosthetic heart valve, which posts are shown in their undeflected condition.
Figure 19:
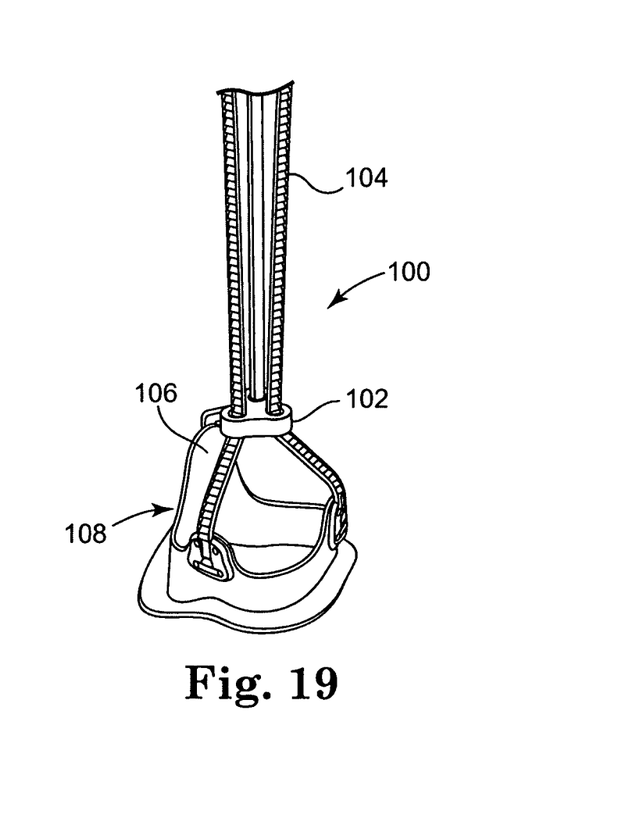
FIG. 19 is a perspective view of the valve holder of FIG. 18, with the stent posts in their deflected condition.

FIGS. 18 and 19 illustrate an alternative embodiment of a valve holder 100 of the invention, which includes a single sliding member 102 that is attached to three extending legs 104. The extending legs 104 are attachable to the top portion of three commissure posts or stent posts 106 of a prosthetic heart valve 108. In this embodiment, a handle (not shown), would be attachable to the top portion of sliding member 102, since an additional connector hub is not provided. FIG. 18 illustrates the stent posts 106 in their undeflected condition, with the sliding member 102 spaced further from the heart valve 108 than in FIG. 19. In FIG. 19, the sliding member 102 has been moved closer toward the heart valve 108, thereby compressing or deflecting the stent posts 106 toward each other. The extending legs 104 may include a similar configuration to that described above relative to extending legs 16, and the sliding member 102 may further include slots that engage with the extending legs 104 in a similar manner to that described above relative to the slots 72a-72c or slots 90a-90c, or the slots may be configured differently. If desired, the ends of the extending legs 104 spaced furthest from the heart valve 108 can be cut once the sliding member 102 has deflected the stent posts 106, in order to keep the free ends from interfering with the implantation procedure.

The valve holders of the present invention may optionally include a mechanism that allows the extending legs to be adjusted independently relative to the sliding member and/or the connector hub, as desired to accommodate a particular patient's anatomy, for example. In addition, the engagement mechanisms (e.g., spring arms and teeth) used to keep the extending legs in place when deflecting the stent posts may also have a mechanism that allows the extending legs to be released or disengaged from the engagement mechanisms. In addition, different ratcheting or sequential advancement types of mechanisms can be used to deflect the stent posts.

Figure 20:
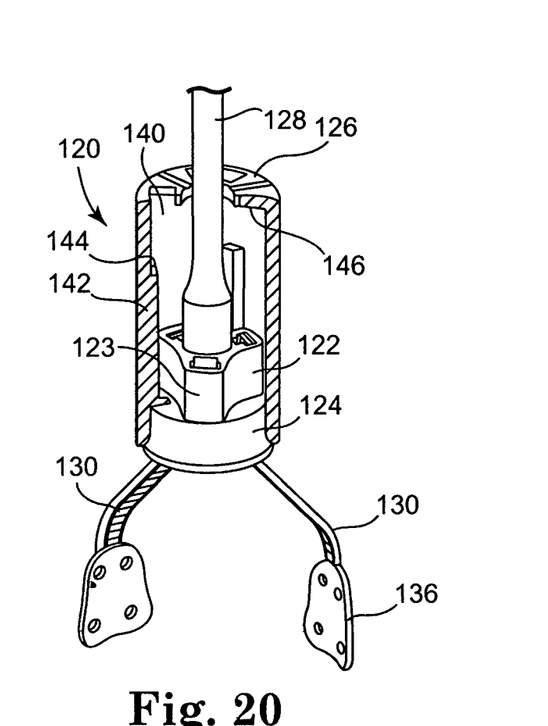
FIG. 20 is a perspective view of another embodiment of a valve holder of the invention, with a cutting sleeve and sliding member in a first position.
Figure 21:
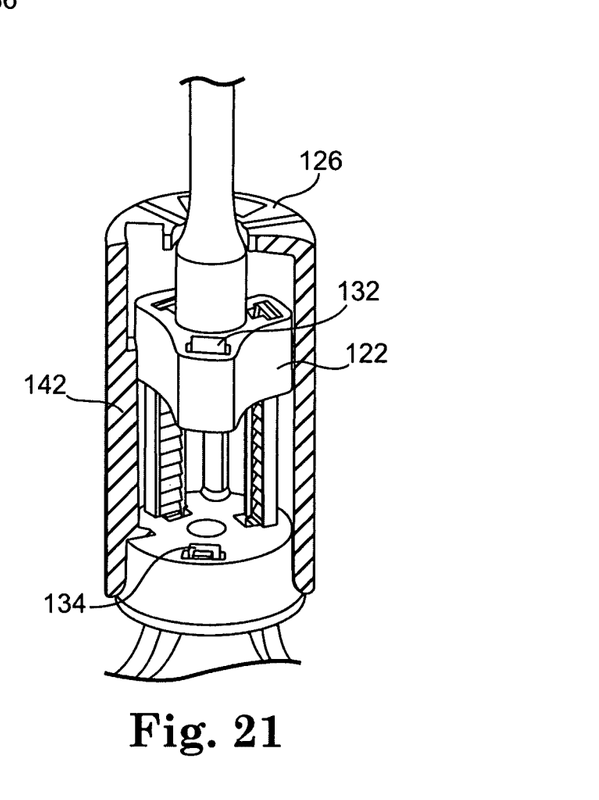
FIG. 21 is a perspective view of the valve holder of FIG. 20 in a second position.
Figure 22:
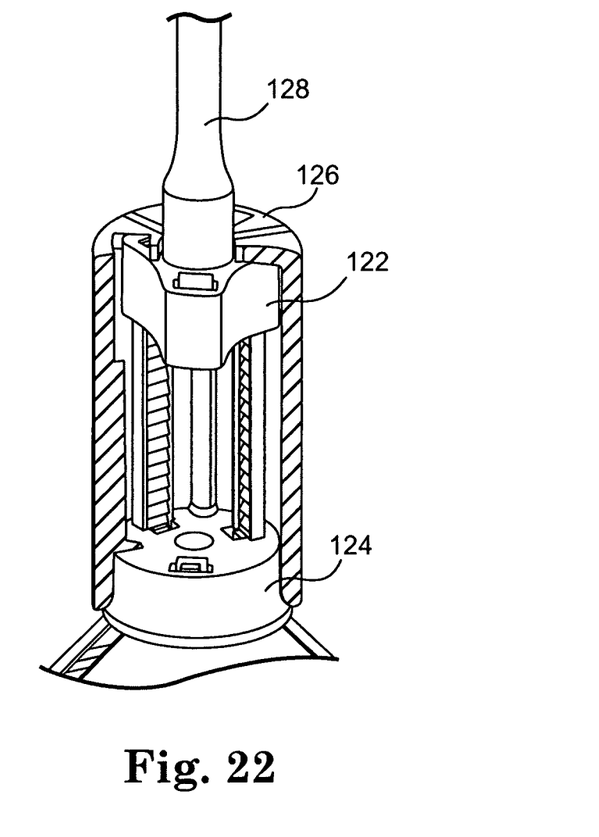
FIG. 22 is a perspective view of the valve holder of FIG. 20 in a third position.

FIGS. 20-22 illustrate another embodiment of a valve holder 120 that generally includes a connector hub 122 having three lobe portions 123, a sliding member 124, and a cutting sleeve 126. A handle 128 extends from one side of connector hub 122 and may include any of the characteristics of handle embodiments described herein, such as attachment configurations (e.g., threaded connections), capabilities for bending and pivoting, materials from which the handle is made, the shapes and sizes of the handle, and the like. Alternatively, other handle embodiments may be used to coordinate with the use of the cutting sleeve 126. In accordance with this embodiment, three extending legs 130 can extend through three corresponding apertures in the connector hub 122 and sliding member 124. However, for clarity of illustration, FIGS. 20-22 show only two extending legs 130, thereby providing a view of one of the apertures 132 in the connector hub 122 and one of the apertures 134 in the sliding member 124.

The extending legs 130 each include a commissure post engaging plate 136 that is attachable to the top portion of a commissure post or stent post of a prosthetic heart valve. The extending legs 130 and engaging plates 136 may include features and configurations similar to those of the extending legs and engaging plates described above relative to FIGS. 5-8. The extending legs 130 of this embodiment are again provided with a plurality of teeth or other engaging members that can lock each leg in a desired positional relationship relative to the apertures 132 and 134 of their respective components. The apertures 132 and 134 may have similar configurations to the slots described above relative to FIGS. 11 and 12, including moveable spring arms for engagement with teeth of an extending leg, or the apertures 132 and 134 may have a different design to accommodate different configurations of the extending legs.

The cutting sleeve 126 includes an inner surface 140 from which multiple cutting ribs 142 extend. In particular, the cutting sleeve of a particular valve holder preferably has the same number of cutting ribs as the number of extending legs of that valve holder. In the embodiment of FIGS. 20-22, the cutting sleeve 126 would therefore have three cutting ribs 142, each of which is positionable in the area between adjacent lobe portions 123 of the connector hub 122. However, only two of the cutting ribs 142 are visible in these particular cutaway views. The cutting ribs 142 each extend along only a portion of the height of the cutting sleeve 126, and each cutting rib 142 has a top surface 144 that is spaced from a top inner surface 146 of the cutting sleeve 126.

In operation, the cutting sleeve 126 is slid over the handle 128, and the handle 128 is connected, such as by a threaded connection, to the connector hub 122 until the handle 128 is secure enough that no spinning or relative motion between the hub 122 and the handle 128 can take place. The cutting sleeve 126 is then oriented to align its cutting ribs 142 with the spaces between adjacent lobe portions 123 of the connector hub 122. The cutting sleeve 126 is slid down over the other components of the valve holder 120 until the bottom surface of the cutting sleeve 126 is generally flush with the sliding member 124. Due to interference between the cutting ribs 142 and the lobe portions 123, the cutting sleeve 126 is restricted from rotating freely around the longitudinal axis of the handle 128. In this configuration, the prosthetic heart valve would be in its uncompressed or expanded condition and the valve holder 120 would generally appear as shown in FIG. 20.

The cutting sleeve 126 can then be slid further downward to push the sliding member 124 toward the commissure post engaging plates 136, thereby causing the extending legs to move through the apertures 134 of the sliding member 124. At the same time, the commissure post engaging plates 136 are moved closer to a longitudinal axis that extends generally through the handle 128. This will cause the corresponding commissure posts to which the engaging plates 136 are attached to move to their compressed or unexpanded configuration. This progression of the valve holder 120 to its compressed configuration is shown generally in FIGS. 21 and 22, where FIG. 22 shows the connector hub 122 at its furthest distance from the sliding member 124, since it essentially "bottoms out" against the top inner surface 146 of the cutting sleeve 126. At this point, the connector hub 122 will be entirely above the top surfaces 144 of the cutting ribs 142.

The heart valve can then be lowered into position within the patient using the handle 128. Once the heart valve and valve holder 120 are in the desired position, the cutting sleeve 126 is rotated so that the cutting ribs 142 can cut the extending legs 130 close to or flush against the sliding member 124. The handle 128, cutting sleeve 126, connector hub 122, and cut portion of the extending legs 130 can then be removed from the patient as a single unit. Portions of this removed unit can be disassembled and discarded or re-sterilized for future use in another procedure. Any suture knots can then be tied in their desired positions within the patient and the remainder of the valve holder 120 can be removed from the patient after cutting the sutures that hold the commissure post engaging plates 136 to the commissure posts of the implanted heart valve.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A valve holder for a prosthetic valve having a stent comprising a stent base and multiple commissure posts projecting from the stent base, the valve holder comprising:
   a connector hub comprising a plurality of slots, wherein each of the slots comprises a one-way sliding mechanism;
   a plurality of legs connected to the connector hub, each leg comprising an elongate portion and a commissure post engaging plate;
   a sliding member slideably connected to each leg of the plurality of legs via at least one one-way sliding mechanism of the sliding member, wherein the sliding member is positioned between the connector hub and the commissure post engaging plates of the plurality of legs and slideably moveable from a first position relative to the connector hub in which the commissure post engaging plates are in an uncompressed configuration to a second position relative to the connector hub in which the commissure post engaging plates are in an at least partially compressed configuration; and
   a handle extending from the connector hub;
   wherein a portion of each of the plurality of legs is positioned within one of the slots of the connector hub.

2. The valve holder of claim 1, wherein the sliding member is closer to the connector hub when the sliding member is in its first position than when the sliding member is in its second position.

3. The valve holder of claim 1, wherein each leg of the plurality of legs comprises a plurality of teeth that can engage with the one-way sliding mechanism of the sliding member.

4. The valve holder of claim 1, wherein each commissure post engaging plate comprises a plurality of apertures spaced from each other to provide suture passages for a stitching sequence.

5. The valve holder of claim 1, wherein the commissure post engaging plate is at the distal end of the elongate portion.

6. The valve holder of claim 5, wherein the commissure post engaging plate comprises a first surface comprising a guide recess positioned generally between two adjacent apertures that can guide a cutting tool to a suture used to attach the commissure post engaging plate to a prosthetic valve.

7. The valve holder of claim 5, wherein the commissure post engaging plate comprises a first surface comprising at least one protective ridge that can guard against undesirably cutting a suture used to attach the commissure post engaging plate to a prosthetic valve.

8. The valve holder of claim 1, wherein the commissure post engaging plate comprises a recess in a second surface of the commissure post engaging plate that has a sufficient size to accommodate a suture knot.

9. The valve holder of claim 1, further comprising three legs spaced from each other around the connector hub.

10. The valve holder of claim 9, wherein the angle between a first leg and a second leg is about 105 degrees, the angle between the second leg and a third leg is about 120 degrees, and the angle between the first leg and the third leg is about 135 degrees.

11. The valve holder of claim 9, wherein three legs are spaced approximately evenly from each other around the connector hub.

12. The Valve holder of claim 1 in combination with a prosthetic valve.

13. The valve holder of claim 1, wherein the sliding member comprises a plurality of slots, and wherein a portion of each of the plurality of legs is positioned within one of the slots of the sliding member.

14. The valve holder of claim 13, wherein each of the plurality of slots of the sliding member comprises one of the one-way sliding mechanisms of the sliding member.

* * * * *